United States Patent [19]

Allen, Jr. et al.

[11] Patent Number: 4,561,858
[45] Date of Patent: * Dec. 31, 1985

[54] OSTOMY BAG WITH INTEGRAL BREATHABLE GASKET

[75] Inventors: Douglas Allen, Jr., Belle Mead; Eric Flam, East Brunswick, both of N.J.

[73] Assignee: C. R. Bard, Murray Hill, N.J.

[*] Notice: The portion of the term of this patent subsequent to Feb. 5, 2002 has been disclaimed.

[21] Appl. No.: 491,256

[22] Filed: May 3, 1983

[51] Int. Cl.⁴ .............................................. A61F 5/44
[52] U.S. Cl. .................................. 604/336; 604/332; 604/338; 604/344
[58] Field of Search ............... 604/277, 317, 336–344, 604/332; 128/284, 287, 290; 428/424.2, 492, 516, 355–356, 447; 260/33.4 R, 874, 901; 424/25, 28

[56] References Cited

U.S. PATENT DOCUMENTS

| | | | |
|---|---|---|---|
| 4,011,871 | 3/1977 | Taft | 128/284 |
| 4,078,568 | 3/1978 | Etes | 128/283 |
| 4,153,055 | 5/1979 | Etes | 128/156 |
| 4,253,460 | 3/1981 | Chen et al. | 128/283 |
| 4,258,715 | 3/1981 | Goble | 128/283 |
| 4,393,080 | 7/1983 | Pawelchak | 428/355 |
| 4,497,914 | 2/1985 | Allen et al. | 523/105 |

*Primary Examiner*—Stephen C. Pellegrino
*Assistant Examiner*—Sherri Vinyard
*Attorney, Agent, or Firm*—Dennison, Meserole, Pollack & Scheiner

[57] ABSTRACT

A new ostomy bag having an integral breathable ostomy gasket derived from the non-aqueous reaction of a polyisocyanate and a polyoxyalkylene polyol moiety having a hydrophilic filler incorporated within the polyol moiety prior to the reaction of the polyisocyanate and the polyol. The bag includes hydrophobic material welded to the bag serving as a backing for the gasket.

5 Claims, 3 Drawing Figures

OSTOMY BAG WITH INTEGRAL BREATHABLE GASKET

BACKGROUND OF THE INVENTION

The present invention relates to ostomy appliances and particularly those devices used by ostomy patients having an integral or unitized thin barrier gasket formed of a composition which has unique and desirable properties, i.e., breathability, tack, resistance to leakage, dissolution, and disintegration by fluids and cohesive strength. More particularly, the invention relates to the combination of a specific gasket material which may be formed as a composite panel with a hydrophobic backing, as for example, a thermoplastic and which is adapted for integral manufacture onto a conventional ostomy appliance such as a colostomy bag or an ileostomy bag.

The present application is a continuation in part of our earlier application, Ser. No. 398,913, filed July 16, 1982, now U.S. Pat. No. 4,497,914 entitled BREATHABLE OSTOMY GASKET COMPOSITION.

The present invention represents major improvements over existing ostomy appliances especially by virtue of the unique combination of properties afforded by the unitized ostomy appliance and a skin barrier. Utilizing the present invention, high levels of conformability, strength and dry and wet adhesion simultaneously and continuously serve to overcome irregularities in the dynamic peristomal region and serve to provide resistance to the leakage of fluids which result in additional comfort to the wearer since there are no flanges or rings as common with many prior art ostomy appliances to interfere with body movements and to present an objectionable appearance beneath clothing.

Ostomy appliance gaskets based upon the inclusion of Karaya powder, as disclosed in U.S. Pat. No. 3,302,647, are currently in general use. Karaya has certain disadvantages since it is a nutrient substance and capable of supporting the growth of micro-organisms, not only in use, but when contaminated in storage prior to use. Karaya compositions are lacking in cohesiveness, and therefore tend to disintegrate as well as become slippery when wet, often times necessitating the use of a special adhesive to prevent dislocation from the ostomy site.

In U.S. Pat. 4,160,076, there are disclosed hydrophilic foams prepared from a capped polyoxyalkylene polyol reactant having a defined average reaction functionality greater than 2, an aqueous reactant and a carefully balanced combination of a nonionic surface-active agent and a liquid defoaming agent. The resultant foams are characterized by a majority of large size cells and membranes which themselves are formed with small cells. In addition, large amounts of many water-soluble or water-dispersable materials such as cellulosic pigments, dyes, enzymes or the like may be added to the aqueous reactant. By homogeneously distributing these materials in the aqueous reactant they may be distributed throughout the finally prepared foam. However, the large cell size and membranes characteristic of the hydrophilic polyurethane sponges do not possess the necessary properties of tack, elasticity, sealability and flexibility needed in an ostomy gasket.

An ostomy gasket possessing varying degrees of tackiness, lubricity, and softness is disclosed in U.S. Pat. No. 3,980,084. The polymeric ostomy sealing gasket therein disclosed is formed by the polymerization of a hydroxyalkyl acrylate or methacrylate in the presence of a polyalkylene glycol, reducing agent, or chain terminator, and water. In manufacturing the gaskets, it is essential that the polymerization reaction be carried out in the presence of water. In this manner, a considerable quantity of water is absorbed into the polymer matrix during the polymerization reaction. In addition, natural or synthetic gums or cellulosic type materials to increase absorptive capacity may be incorporated into the polymer matrix. However, the material disclosed has a very low elongation at break and will not return to its original shape after deformation. In addition the materials are often highly viscous and therefore lack the sealability preferred for use in an ostomy device which may result in leakage around the ostomy seal.

OBJECTS OF THE INVENTION

One of the principal objects of the present invention is to provide a new unitized ostomy appliance having a built in seal formed from a special gasket composition.

A further object of the invention is the provision of a unitary ostomy bag and seal which may be manufactured utilizing conventional techniques and which offers great comfort to the wearer and ease in application.

Another object of the invention is realized by providing a polymeric composition adapted for use in contact with the skin derived from the non-aqueous reaction of a polyisocyanate and a polyoxyalkylene polyol moiety having a hydrophilic filler physically incorporated within the polyol prior to the reaction.

A further object of the invention is found in the physical characteristics of the polymeric composition of the present invention, which composition provides a seal between the ostomy device and skin (epidermis) of the human body having a high degree of tack, elasticity, flexibility, and resistance to body fluids. This precludes movement of the seal around the stomal opening which can result in leakage of body material thereby causing irritation and excoriation if allowed to come into repeated or continuous contact with the skin.

Another object of the invention is to the cohesive conformability of the new composition. This property enables the composition to be molded in preferred shapes which inherently adheres to both the patient's skin and the collection receptacle without the use of additional adhesives. The new composition is soft and resilient, minimizing discomfort to the wearer of an ostomy appliance.

Yet another object of the invention is to extend the shelf life and resistance to contamination of the new composition over Karaya products which have limited shelf life and harden during storage.

SUMMARY OF THE INVENTION

A sealing pad or gasket formed of the composition of our earlier application is interposed between a fluid resistant material, such as a fabric, film, non-woven fabric, or the like which is welded to the face of the ostomy device and the skin of the user surrounding the stoma. The sealing pad serves to contain the waste fluids that are highly irritating to the skin and which may contain microorganisms of the intestinal tract, and which also give off offensive odors. Additionally, the sealing pad assists in retaining the appliance in place and makes the appliance more comfortable to wear.

The sealing pad of the invention is especially adapted for performing the foregoing functions. Owing to its composition, the pad may be cast in any desirable configuration, and it will retain its shape and not break apart in use.

The composition for forming the pad or gasket is prepared by the reaction of an organic polyisocyanate with one or more di or polyfunctional hydroxyl compounds for example polyoxyalkylene polyols such as those derived from propylene or ethylene oxide, preferably having equivalent weights of at least 500. A hydrophilic filler, such as a cellulosic or natural gum, is incorporated into the polyol moiety of the urethane system prior to the reaction of the polyols with the polyisocyanate moiety.

The soft polymeric matrix or adhesive composition that is formed by the reaction physically encapsulates the uniformly dispersed hydrophilic filler within the resulting self-sustaining adhesive composition. Thus, the product resists swelling and dissolution by or passage of bodily fluids while being inherently breathable thereby readily allowing migration and transfer of gases such as water vapor.

Our new ostomy bag which may be formed, for example, either as an ileostomy pouch, urostomy pouch, or colostomy bag utilizes the highly elastic, tacky, rubbery gum of our earlier application, Ser. No. 398,913, as the gasket material and the same is backed with a soft, fluid resistant material and is cast with sufficient thinness to allow the backing to be firmly welded or otherwise secured in an integral fashion to the plastic film of the ostomy appliance directly through the gasket.

DETAILED DESCRIPTION OF THE INVENTION

Figure 1:
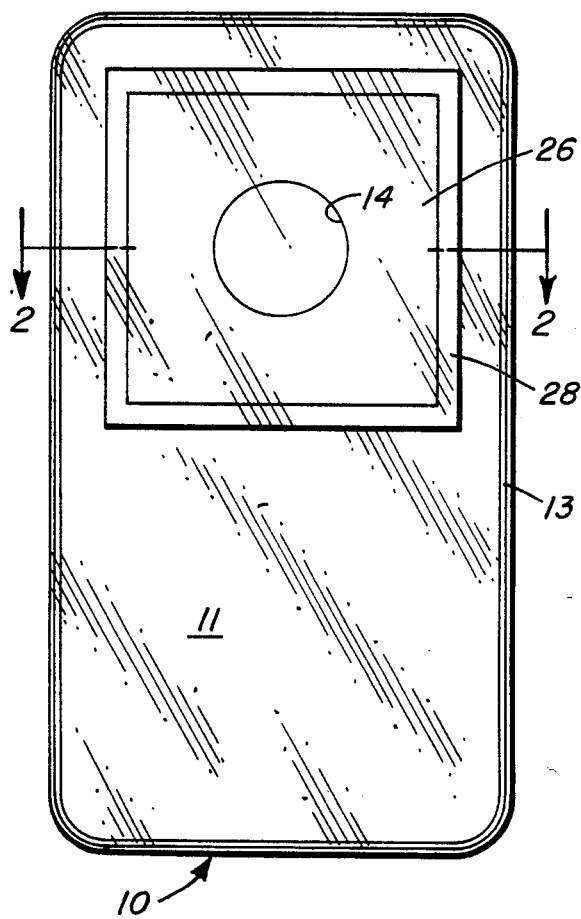
FIG. 1 is a plan view of a typical colostomy bag of the present invention.

Further objects and advantages will become apparent from a consideration of the drawings and this detailed description wherein like reference characters refer to similar parts throughout the description.

The invention herein disclosed consists of a unitary assembly of an ostomy bag shown generally at 10 which may be formed in any of several well-known configurations. The bag in FIG. 1 represents a typical colostomy bag of the type that that are normally used after surgery. A surgical procedure such as a colostomy, ileostomy, or urostomy consists of the formation of an opening, or stoma in the wall of the intestine or colon, which opening extends through the wall of the patient's skin. A urostomy consists of either bringing the ureters to the abdominal skin (ureterostomy) or connecting the ureters to a section of the ileum which in turn is brought out to the skin (ileal-conditut). The stoma provides means for communication between the inside of the organ and the external area through which various bodily excretions may pass. Therefore, it is necessary for the post-surgical patient to wear a collection receptacle for this material such as a pouch or bag attached to the stoma. It is further important that there be a seal between the patient's skin and the collection receptacle. Especially due to the noxious nature of the waste material which passes through the stoma, it is desirable that none of the materials be allowed to leak past the seal since these materials are irritating to the skin and can cause irritation if allowed to come into repeated contact therewith. The bag as shown in FIG. 1 or receptacle is formed of flexible water-impervious material such as polyethylene or polypropylene film or sheet material having spaced walls 11 and 12 which are preferrably heat sealed at their edges as indicated at 13. An opening 14 is provided at an appropriate position on the front wall 11. This opening varies depending upon the particular stoma and can be for example from 12 to 65 millimeters in diameter.

Figure 3:
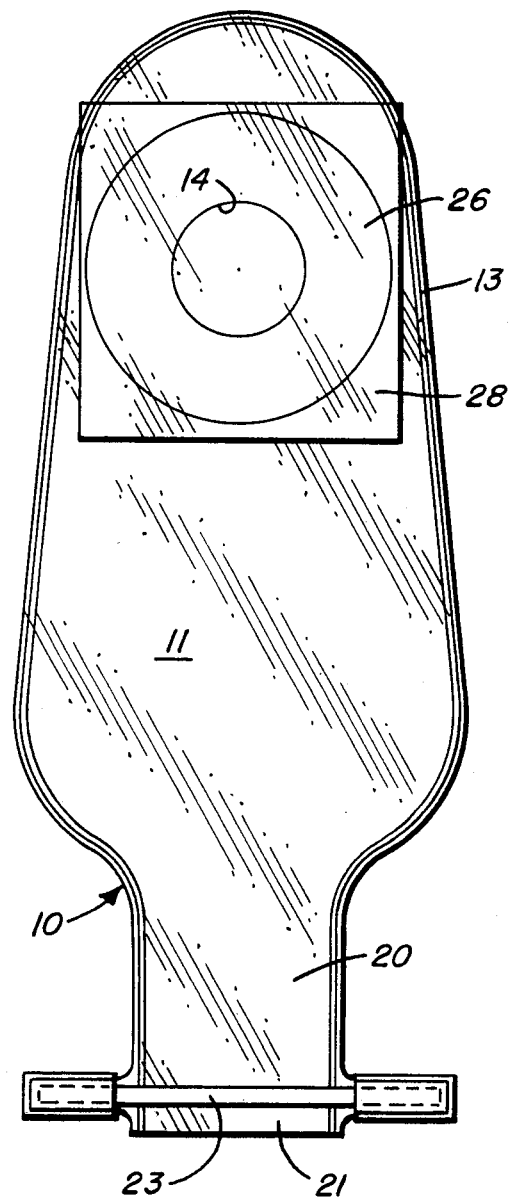
FIG. 3 is a plan view of a typical ileostomy pouch utilizing the present invention.

With regard to the ileostomy container of FIG. 3, the bag is generally formed in the same manner although the shape may vary and there is usually means at the bottom thereof to permit emptying of waste liquid material. In this manner the pouch or bag can remain on the body for several days. In the FIG. 3 embodiment, the bag has a narrow bottom portion shown at 20 and the end thereof 21 is open but may be sealed by use of the flexible clip 23 which is secured thereto. In use, the bottom portion 20 is rolled upwardly and the flexible clip 23 is bent over in a well-known manner to close the exit port 21. Here again an opening 14 is provided.

Figure 2:
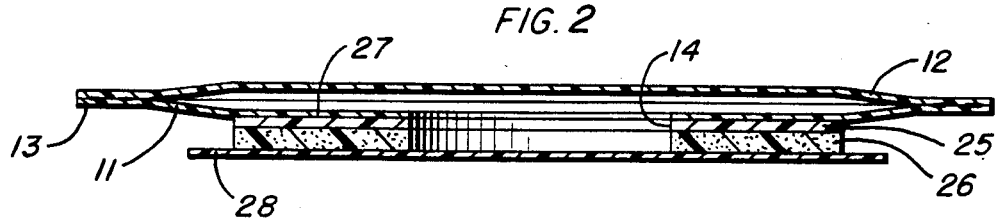
FIG. 2 is an enlarged cross sectional view through the bag of FIG. 1 taken along the lines 2—2 thereof.

In order to attach the appliance to the body it is necessary to provide a tacky seal or a gasket. Here a thin patch of material shown at 25 is employed and the same consists of a fluid resistant, hydrophobic material as previously described. The material is quite thin, generally less than 0.050 inches, preferrably about 0.010 inches but also as low as 0.001 inches in thickness. The highly elastic, tacky, rubbery gum which is described in greater detail later herein is applied to the fabric backing 25 and is shown in FIG. 2 at 26. Here the material is applied in a thickness of from about 0.010 inches to 0.050 inches. Heat sealing of the gasket 26 and backing 25 may take place directly through the gasket material and a firm secure weld will be insured as shown at 27.

In order to protect the gasket 26 prior to use, a thin sheet of peelable material such as release paper or film, 28 is applied over and adheres to the tacky gasket. This serves to guard the gasket in storage and prevents adherence thereto of dust or other foreign particles. It is gripped at a free edge and readily torn off and discarded prior to the application of the appliance.

The polyisocyanates used in preparing the gasket compositions of the present invention are represented by the formula R(NCO)n where n is at least 2, and R is selected from the group consisting of aliphatic, alicyclic, aliphaticalicyclic, aromatic or aliphatic-aromatic hydrocarbon compounds.

Examples of commercially available polyisocyanates which may be used include liquid isocyanates or polymeric isocyanates based on 4,4' methyldiphenyldiisocyanates such as UpJohn Company Isonate 143L, UpJohn Company PAPI 901, Mobay Chemical Corporation Mondur CD, and Mobay Chemical Corporation Mondur MRS-10.

Among the commercially available polyoxyalkylene polyols which may be utilized in the practice of the invention are, for example, Niax Polyol-PPG-3025 (Union Carbide Corporation), Poly-G 55-37 (Olin Chemicals), Poly-G 85-28 (Olin Chemicals), and Multranol 3901 (Mobay Chemical Corporation).

The preferred polyols are Union Carbide Niax Polyol-PPG-3025 and Mobay Multranol 3901. The preferred polyisocyanate is UpJohn Company Isonate 143L.

The proportions and molecular weights of the polyoxyalkylene polyols used, as well as the amounts of the hydrophilic fillers, are governed by the desired characteristics of the final product. Thus, one may tailor products having a diverse range of properties such as tackiness, breathability, cohesiveness and the like.

For example, an elastomer matrix composition formed with diol moieties having nominal equivalent weights of 1500 and triol moieties having nominal equivalent weights of 2000, used in a ratio of approximately 4 to 1 (by equivalents) of diol to triol, yields a particularly desirable product for an ostomy sealing gasket having physically incorporated therein a hydrophilic filler such as hydroxyethylcellulose, hydroxypropyl cellulose or mixtures thereof in the range of approximately 20 to 50% by weight of the final plastic composition.

It has been found that substantially more breathable products are obtained with the use of hydroxyethylcellulose and hydroxypropylcellulose than, for example, with sodium carboxymethylcellulose, karaya gum or polyacrylamide based polyelectrolytes.

In making the breathable elastomeric materials used in this invention, the polyol moieties are blended with the hydrophilic filler or fillers to form a homogenous mixture, the consistency of which may vary from a thin cream to a paste. The mixture is then reacted with the polyisocyanate moiety. Techniques such as a one-shot or prepolymer reaction procedure may be employed.

In the prepolymer reaction procedure, the polyol moiety is reacted with an isocyanate to yield longer chains having terminal NCO groups which may later react with additional polyol moieties. This defines in part the physical characteristics of the resulting plastic composition.

For example, the elastomeric matrix product tends to become harder and less conformable as the cross-link density of the structure increases, as for example, with higher functionality polyol and/or NCO moieties. These physical characteristics also are evident if the molecular weight of the polyol moiety is decreased. The reverse is true, in that as the molecular weight of the polyol moiety is increased, the composition tends to become softer and weaker.

In addition, the stoichiometry affects the final composition as follows. When the NCO/OH ratio is increased, there is a reduction in conformability and tack, while a decrease in the NCO/OH ratio yields a product with increased tack, but decreased strength.

The reaction is catalyzed by known catalysts for such reactions. Suitable catalysts include organic tin esters such as dibutyltindilaurate, tertiary amines, and other catalysts well known in the art.

In addition, a suitable surfactant, such as Dow Corning Antifoam B may be utilized to aid in controlling the uniformity of flow and formation of the resulting plastic compositions.

Many suitable adhesive compositions can be obtained by minor variations in the amounts of ingredients employed. The following examples are illustrative of the invention.

EXAMPLE 1

35.0 grams (0.0233 equivalents) of Union Carbide Niax Polyol PPG 3025 (1500 Equivalent Weight polyether diol) and 11.0 grams (0.0055 equivalents) of Mobay Multranol 3901 (2000 EW polyether triol) were blended with 2 drops of M & T Chemical Catalyst T-12 (dibutyltindilaurate) and 1 drop Dow Corning Antifoam B (silicone surfactant). To this mixture, 24.0 grams of Hercules Natrosol 250 HHR hydroxyethylcellulose were blended to form a smooth, homogeneous, creamy liquid.

Then, 4.2 grams (0.0292 equivalents) of Upjohn Isonate 143L (liquid isocyanate based on 4,4' methyldiphenyldiisocyanate) were added and the mixture thoroughly blended for 60-90 seconds, after which it was poured into an open ⅛" deep sheet mold constructed from silicone release paper. The mixture was allowed to cure until set at room temperature for 1 hour and then cured overnight at 45 C.

The resulting product was a soft, flexible, tacky elastomer that is light tan in color and possesses high elasticity and conformability. It is breathable and highly durable to body fluids. This combination of properties is ideally suited for use as an ostomy barrier.

EXAMPLE 2

The procedure of Example 1 is repeated, except that the silicone surfactant was deleted. The resulting product was identical to that of Example 1.

EXAMPLE 3

The procedure of Example 1 was repeated using 28.8 grams (0.0192 equivalents) of PPG 3025 and 19.2 grams (0.0096 equivalents) of Multranol 3901.

The resulting product was similar to Example 1, however somewhat lower in tack and elasticity.

EXAMPLE 4

The procedure for Example 1 was repeated using 21.6 grams (0.0144 equivalents) of PPG 3025 and 28.8 grams (0.0144 equivalents) of Multranol 3901.

The resulting product possessed less tack and elasticity than Example 3.

EXAMPLE 5

The procedure for Example 1 was repeated using 43.2 grams (0.0288 equivalents) of PPG 3025 and no Multranol 3901 with 40 drops of catalyst T-12.

The resulting product was highly tacky and soft, exhibiting creep, and not suitable for an ostomy gasket.

EXAMPLE 6

The procedure for Example 1 was repeated using no PPG 3025 and 57.6 grams (0.0288 equivalents) of Multranol 3901.

The resulting product tears easily and has low conformability and tack rendering it unsuitable as an ostomy gasket.

EXAMPLE 7

The procedure for Example 1 was repeated using 36.4 grams (0.0243 equivalents) of PPG 3025 and 9.0 grams (0.0045 equivalents) of Multranol 3901.

The resulting product was very soft and tacky exhibiting a slight tendency to creep.

EXAMPLE 8

The procedure for Example 1 was repeated using 11.7 grams (0.0233 equivalents) of Quaker Oats Polymeg 1000 (500 EW polytetramethylene ether glycol) and 11.0 grams (0.0055 equivalents) of Multranol 3901.

The resulting product had lower conformability, tack, elasticity, and tear strength than Example 1.

EXAMPLE 9

The procedure for Example 1 was repeated using 13.0 grams Hercules Klucel HF hydroxypropylcellulose in place of Natrosol.

The resulting product was whiter than but otherwise similar to Example 1.

EXAMPLE 10

The procedure for Example 1 was repeated using 16.0 grams Natrosol 250 HHR and 8.0 grams Klucel HF.

The resulting product was lighter colored than Example 1 but otherwise similar in properties.

EXAMPLE 11

The procedure for Example 1 was repeated using an initial cure at 45 C. for 15 minutes to set the material followed by overnight cure at room temperature.

The resulting product is similar to Example 1.

EXAMPLE 12

A prepolymer was prepared by mixing 35.0 grams (0.0233 equivalents) of PPG 3025 with 11.0 grams (0.0055 equivalents) of Multranol 3901 and drying the mixture at 100–110 C. under vacuum at 30 in. Hg.

8.4 grams (0.0584 equivalents) of Isonate 143L were added slowly with thorough mixing and the mixture maintained at 95 C. for 4 hours under nitrogen with frequent mixing. It was then set aside under a nitrogen lid at room temperature until the following day, when a homogeneous mixture of:

35.0 grams (0.0233 equivalents) of PPG 3025,
11.0 grams (0.0055 equivalents) Multranol 3901,
4 drops of T-12 (dibutyltindilaurate),
2 drops antifoam B, and
48.0 grams Natrosol 250 HHR was added. The mixture was thoroughly blended for 60–90 seconds and poured into a sheet mold as in Example 1, cured at room temperature for 1 hour and then at 45 C. overnight.

The resulting product was identical to Example 1.

EXAMPLE 13

A quasi-prepolymer was prepared by mixing 10 grams (0.0694 equivalents) of Isonate 143L into 10 grams (0.0066 equivalents) of PPG 3025 (previously dried at 100–110 C. under vacuum at 30 in. Hg.). The mixture was maintained under nitrogen at 95 C. for 4 hours with frequent mixing, after which it was set aside under a nitrogen lid at room temperature until the following day.

At that time, 8.4 grams of the quasi-prepolymer were added to a homogeneous mixture consisting of the following:

30.8 grams (0.0205 equivalents) PPG 3025
11.0 grams (0.0055 equivalents) Multranol 3901
4 drops T-12
2 drops Antifoam B
24.0 grams Natrosol 250 HHR The mixture was thoroughly blended for 60–90 seconds and poured into a sheet mold as in Example 1, cured at R.T. for 1 hour, then at 45 C. overnight.

The resulting product was identical to Example 1.

We claim:

1. An ostomy bag having a front face provided with a stoma opening therein, a backing of hydrophobic material welded to said front face surrounding said opening, and a skin barrier gasket on the exposed face of the backing, said skin barrier gasket being a polymeric composition comprising a product derived from the generally non-aqueous reaction of an organic polyisocyanate, and a polyoxyalkylene polyol moiety comprising a mixture of a major portion of polyol having a diol functionality and a minor portion of polyol of at least triol functionality, and having incorporated into the polyol moiety prior to the generally non-aqueous reaction of the polyisocyanate and the polyol moiety a hydrophilic filler wherein there is provided a polymeric matrix characterized by the physical encapsulation of the hydrophilic filler within the polymeric matrix.

2. An ostomy bag as defined in claim 1, wherein the hydrophobic backing is a fluid resistant material.

3. An ostomy bag as defined in claim 1 wherein said polyol consists of diols of nominal equivalent weights of 1500 and triols of nominal equivalent weights of 2000 in a ratio of approximately 4 to 1 of diol to triol.

4. An ostomy bag as defined in claim 1, wherein said polyisocyanate is a liquid ioscyanate based on 4,4' methyldiphenyldiisocyanate;
   said polyol is a mixture of 1500 equivalent weight polyether diol and 2000 equivalent weight polyether triol.

5. An ostomy bag as defined in claim 1, wherein the polymeric composition comprises a product derived from the generally non-aqueous reaction of an organic polyisocyanate of the formula $$R(NCO)_n$$

where R is selected from the group consisting of aliphatic, alicyclic, aliphatic-alicyclic, and aromatic or aliphaticaromatic hydrocarbon compounds and n is at least 2, and a polyoxyalkylene polyol moiety of the formula $$R(OH)_{n'}$$

where R is a polyoxyalkylene and n' is at least 2, the polyol moiety comprising a mixture of a major portion of polyol having a diol functionality and a minor portion of polyol of at least triol functionality, and having incorporated into the polyol moiety prior to the reaction of the polyisocyanate and the polyol moiety, a hydrophilic filler wherein there is provided a polymeric matrix characterized by the physical encapsulation of the hydrophilic filler within the polymeric matrix.

* * * * *